(12) United States Patent
Pankin et al.

(10) Patent No.: US 8,470,031 B2
(45) Date of Patent: Jun. 25, 2013

(54) DEVICE FOR FOLDING OR ROLLING AN INTRAOCULAR LENS TO BE IMPLANTED INTO AN EYE

(75) Inventors: Dmitry Pankin, Munich (DE); Hans-Jurg Kreiner, Munich (DE)

(73) Assignee: Carl Zeiss Meditec AG, Jena (DE)

(*) Notice: Subject to any disclaimer, the term of this patent is extended or adjusted under 35 U.S.C. 154(b) by 543 days.

(21) Appl. No.: 12/443,812

(22) PCT Filed: Sep. 19, 2007

(86) PCT No.: PCT/EP2007/008150
§ 371 (c)(1), (2), (4) Date: Sep. 30, 2010

(87) PCT Pub. No.: WO2008/040446
PCT Pub. Date: Apr. 10, 2008

(65) Prior Publication Data
US 2011/0015644 A1   Jan. 20, 2011

(30) Foreign Application Priority Data
Sep. 29, 2006 (EP) ..................... 06020639

(51) Int. Cl.
*A61F 9/00* (2006.01)
(52) U.S. Cl.
USPC ....................................... 623/6.12

(58) Field of Classification Search
USPC .................. 606/107; 623/6.12; D24/150
See application file for complete search history.

(56) References Cited

U.S. PATENT DOCUMENTS

| | | | |
|---|---|---|---|
| 4,681,102 A | 7/1987 | Bartell | |
| 2002/0103490 A1 | 8/2002 | Brady | ............ 606/107 |

FOREIGN PATENT DOCUMENTS

| | | |
|---|---|---|
| DE | 10164420 A1 | 7/2003 |
| EP | 1 114 623 A1 | 7/2001 |
| EP | 1 466 571 A1 | 10/2004 |
| WO | 99/29267 A1 | 6/1999 |
| WO | 03/044946 A2 | 5/2003 |
| WO | 2005/082285 A1 | 9/2005 |

OTHER PUBLICATIONS

International Search Report for PCT/EP2007/008150, mailed May 12, 2008, 6 pages.

*Primary Examiner* — Elizabeth Houston
(74) *Attorney, Agent, or Firm* — Robert Iannucci; Seed IP Law Group PLLC

(57) ABSTRACT

A device for folding or rolling up an intraocular lens 1 that is to be implanted into an eye, with a lens receiving compartment 2 that is formed by two swivel-connected lens receiving parts 3, 4, which lens receiving compartment 2 is to be moved from an open position for receiving the lens 1, in which the lens is unfolded, into a closed position for folding or rolling up the lens 1 by swiveling the lens receiving parts 3, 4 relative to each other, and with a holding device which is formed by two holding elements 5, 6, one of which holding elements 5 is attached to one lens receiving part 3 and the other holding element 6 is attached to the other lens receiving part 4.

18 Claims, 4 Drawing Sheets

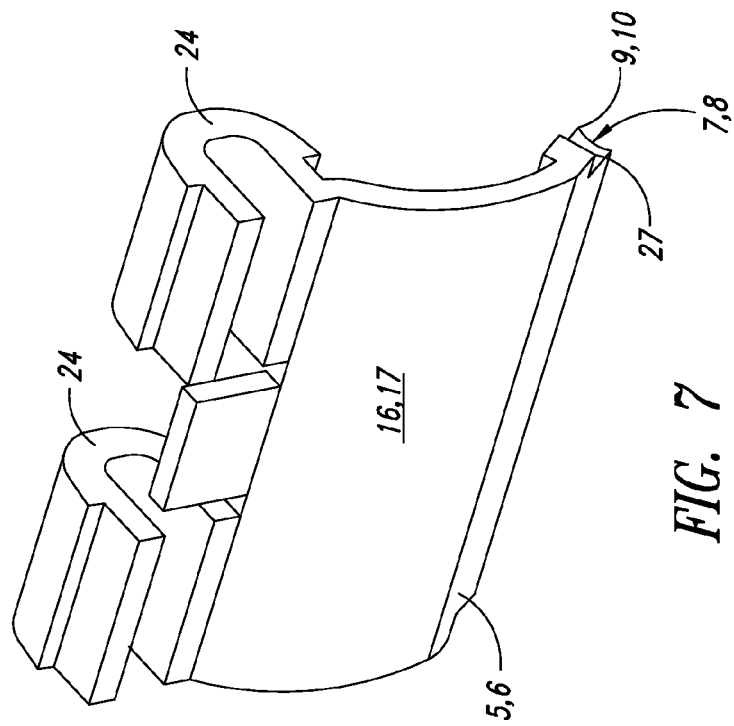
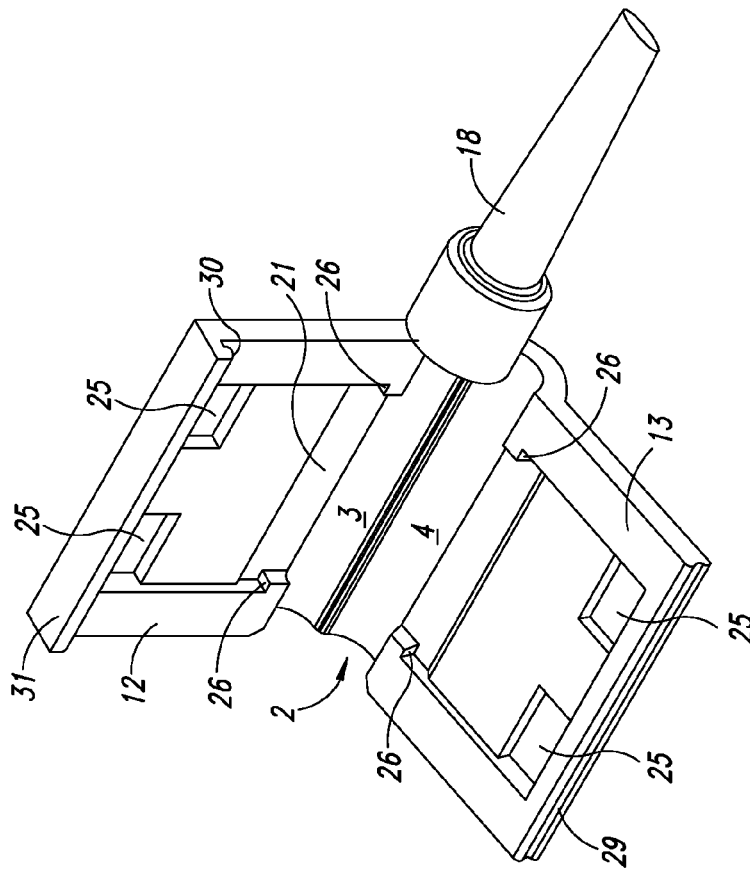

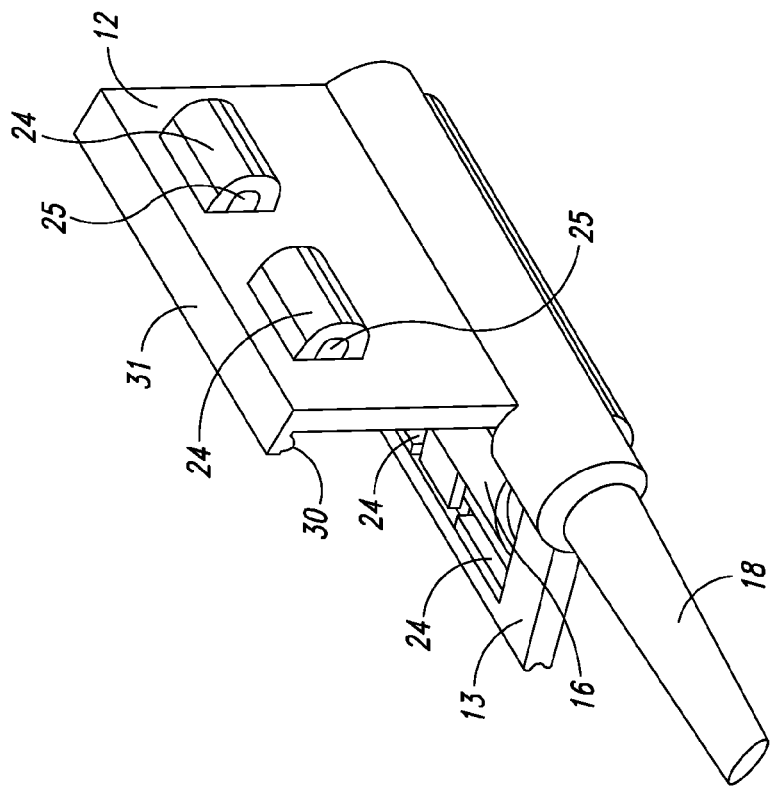
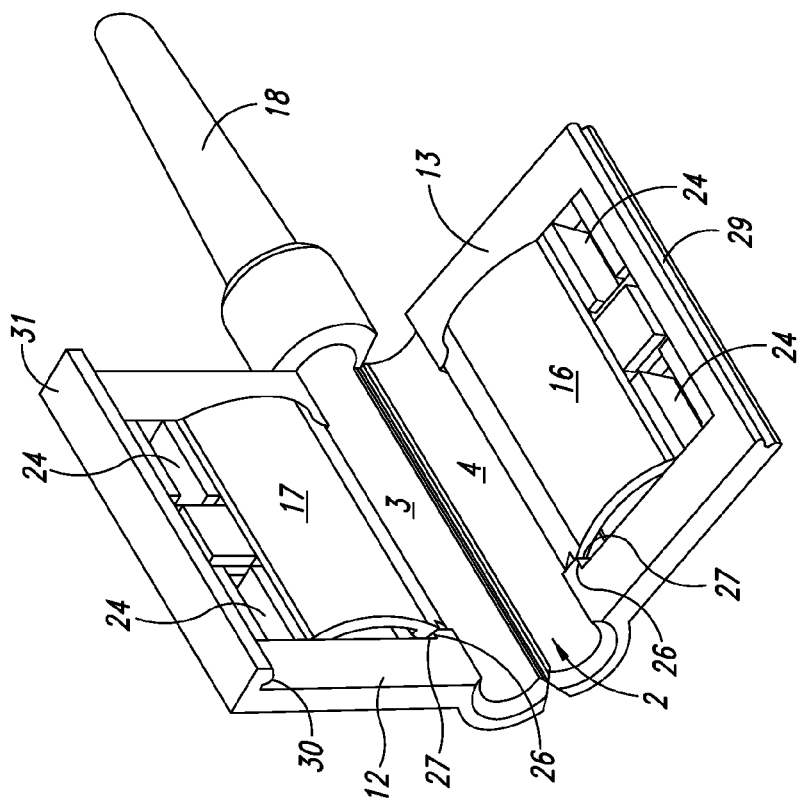
FIG. 9
FIG. 8

DEVICE FOR FOLDING OR ROLLING AN INTRAOCULAR LENS TO BE IMPLANTED INTO AN EYE

The present invention relates to a device for folding or rolling up an intraocular lens that is to be implanted into an eye as defined in the precharacterizing clause of Claim 1.

This type of device which is known from DE 101 64 420 A1 comprises two swivel-connected half plates which can be swiveled from an open starting position for receiving the unfolded lens into a closed end position for folding or rolling up the lens. In this closed position, the lens receiving compartment forms a guide channel which, in the direction of implantation, is open on both ends and from which the lens to be implanted can be implanted into the eye through an injection cannula that is inserted into an eye by means of an injector plunger. To hold the intraocular lens, in particular while it is being folded, a film-like loop is provided, one end of which is attached to one of the two half plates and movably guided along the second half plate. In the open starting position, the receiving chamber for the intraocular lens is formed between the loop and the two half plates. To make the folding movement easier, i.e., to move the two half plates from the open starting position into the end position, the half plates are fitted with wings which can be manipulated by hand.

The device known from U.S. Pat. No. 4,681,102 also has wings on the two half plates that form the lens receiving compartment, which wings are used to swivel the half plates from the open starting position into the closed end position. This prior-art device again is used as a cartridge in an injector, by means of which the folded lens is implanted into the eye through an injection cannula by means of a plunger. This prior-art device does not comprise a holding device, which means that when the lens is being folded, there is a risk that the lens, due to its resilient properties, is not sufficiently stably held between the half plates and therefore can accidentally slip on its own out of the open or still partially open lens receiving compartment.

The problem to be solved by the present invention is to make available a device of the type mentioned above, by means of which the intraocular lens can be more easily loaded into the open lens receiving compartment, with the lens that is disposed in the lens receiving compartment being securely positioned when the lens receiving compartment is open and when the lens is being folded.

This problem is solved according to the present invention by the features of claim 1, with useful improvements of the invention being offered by the dependent claims.

According to this invention, the holding device comprises two holding elements which are attached to the two swivel-connected lens receiving parts. Each holding element has a stop face which lies diametrically opposite to edge regions of the unfolded lens when said lens lies in the open lens receiving compartment and which prevents the lens from moving out of the lens receiving compartment. When the receiving compartment is closed, the stop faces are moved into such positions that they enclose the lens receiving compartment preferably flush with the boundary surfaces formed by the lens receiving parts. The intraocular lens located in the closed lens receiving compartment is folded or rolled up. When folded or rolled up, the intraocular lens is in an accurately defined position which is reproducible. This ensures that during implantation, the lens, in the position desired, can be removed from the lens receiving compartment and be inserted into the eye. The lens material can be compressed into such a state that the lens material is more rigid when it is propelled into the direction of implantation, especially in the area in which the propelling plunger and the lens make contact. As a result, it is possible, by means of an injector, to implant the lens through extremely small incisions, e.g., of 1.5 mm to 1.9 mm, into the eye. Consequently, the present invention is preferably used with elastic lenses of the MICS (Micro Incision Cataract Surgery) type. To facilitate the propulsive movement of the lens, a viscoelastic solution which improves the gliding ability of the lens as known from the prior art can be used.

While the lens receiving parts are being swiveled relative to each other, preferably a pressure generated by the holding elements on the stop faces is exerted on the diametrical edge regions of the lens, which causes the initially loose-lying intraocular lens to be laterally pushed toward the center of the lens.

In addition, the stop faces may have inside edges which run substantially parallel to the longitudinal center of the lens to be folded. These inside edges are located at a specific distance from the diametrical edges of the lens, which distance can measure approximately 1 mm. As the lens receiving parts are swiveled toward each other, these edges exert a pressure on the lens in the direction of the bottom or the inside of the lens receiving compartment so that, as a result of the factors acting on the lens body, the folding of the lens about the longitudinal center of the lens is initiated. As the lens receiving parts continue to be moved toward each other, the elastic intraocular lens is forced to fold or roll up in the desired position within the lens receiving chamber. At the same time, the stop faces on the lens holding parts are moved from an upper or outer position into the lower or inner end position in which the stop faces, in cooperation with the boundary surfaces that are formed on the lens receiving parts, ensure a preferably flush enclosure of the lens receiving compartment. At the same time, the intraocular lens is pushed from the direction of the diametrically located edges downward into the folded or rolled-up position.

The two holding elements are preferably designed so as to be resilient and can be attached to wings, by means of which the lens receiving parts can be swiveled relative to each other while the lens is being folded. To this end, the inside surfaces of the wings can be fitted with points of attachments for the holding elements, for example, with a form-fitting locking means, clamp-fitting locking means, hinges or the like. Between these attachment points and the stop faces, the holding elements preferable comprise bent parts which are responsible for the resilience of the holding elements. As the wings are moved toward each other, the bent parts of the holding elements are also moved toward each other and touch each other. As the wings continue to close, the bent parts are stretched to form linear parts, with the stop faces on the holding elements causing the above-explained movement of the stop faces from an outer position into an inner position. To this end, the stop faces are preferably guided in recesses on the wings and/or lens receiving parts.

Stops, on which the holding elements are supported when the lens receiving compartment is closed, are preferably disposed on the lens receiving parts or on the wings in close vicinity to the lens receiving compartment. To this end, the holding elements have associated stops as well. In this manner, it is possible to accurately position the stop faces when the lens receiving compartment is closed so that a flush inner boundary surface is formed in the lens receiving compartment. Manufacturing tolerances in the production of holding elements which are preferably made of a plastic material, for example, by means of injection molding, do not have a negative effect since the space between the stop faces and the stops is very small. Tolerances are compensated for in the region of the bent parts of the holding elements or as a result of the resilient properties of the holding elements.

The lens receiving parts which form the lens receiving compartment are preferably components of a cartridge which can be inserted into an injector or which is disposed on the injector. The ends of the lens receiving compartment that face in the direction of implantation are open, and one of these ends opens out into an injection cannula while through the other open end, a propelling plunger which pushes the intraocular lens in the direction of implantation can be moved.

The cartridge can be designed in such a way that the intraocular lens, which, by means of the holding device, is supported in an unfolded and tension-free state in this cartridge, can be sterilized and stored, for example, in readiness for shipment and transport. By subsequently using a simple maneuver, such as swiveling the lens receiving parts in the direction toward each other, the intraocular lens contained in the cartridge can be folded and shaped into the folded or rolled-up condition needed for implantation. Thus, the cartridge serves as a storage container for the lens which is stored unfolded and tension-free in readiness for use in this cartridge and, furthermore, as a folding device for the lens by means of which the lens is made to assume the shape suitable for implantation. For transportation and/or storage of the lens, the holding device or cartridge can be sterilely disposed in a container or a sleeve.

Practical examples of the invention will be explained in greater detail below with reference to the figures of the accompanying drawing. As can be seen:

FIG. 6 shows a perspective view of another practical example of the present invention which is also designed in the form of a cartridge which is open;

FIG. 7 shows a perspective view of a holding element, two of which are to be mounted in the practical example of FIG. 6;

FIG. 8 shows the practical example of the invention in the mounted state in which the components shown in FIGS. 6 and 7 are used, with the line of vision toward the inside of the lens receiving compartment; and FIG. 9 shows a perspective view of the back of the practical example seen in FIG. 8.

The figures show practical examples of a device for folding or rolling up an intraocular lens 1. The practical examples comprise a lens receiving compartment 2 which is formed by two lens receiving parts 3, 4. The lens receiving parts 3, 4 are swivel-connected to each other. The lens receiving parts 3, 4 have the shape of cylinder segments and are swivel-connected along a longitudinal swivel axis.

Figure 3:
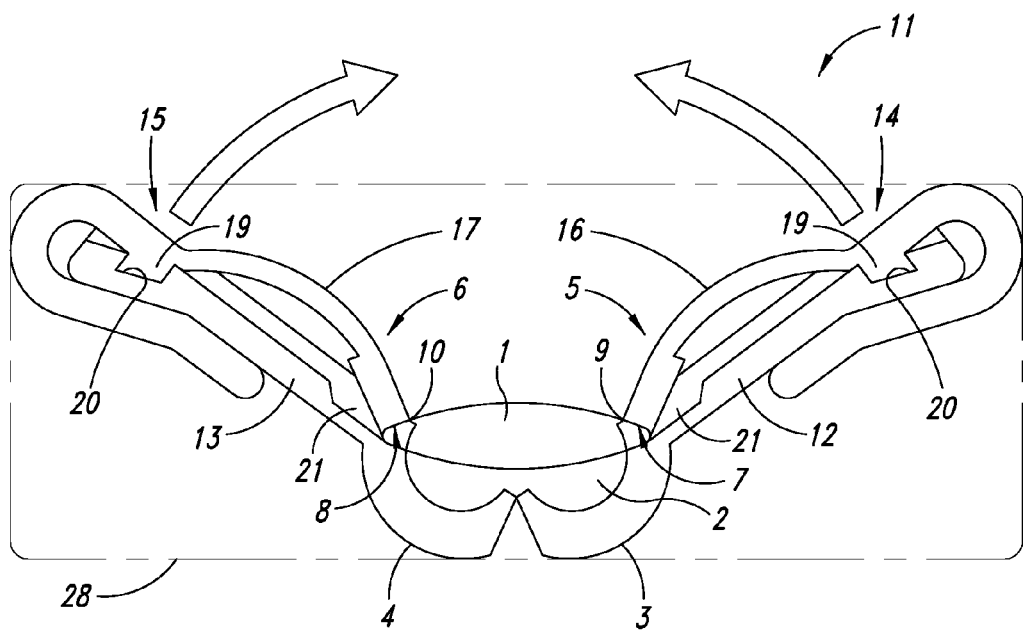
FIG. 3 shows a sectional view of a starting position of the lens receiving compartment for folding the intraocular lens.

Wings 12, 13 are either attached to or molded in one piece with the lens receiving parts 3, 4. When the intraocular lens 1 is being folded, the wings 12, 13 are moved toward each other, as indicated in FIG. 3 by the arrows that point at each other. In the course of this folding procedure, the initially unfolded and tension-free intraocular lens 1 located in the lens receiving compartment 2 is folded, as will be explained in greater detail with reference to FIGS. 4 and 5.

Figure 1:
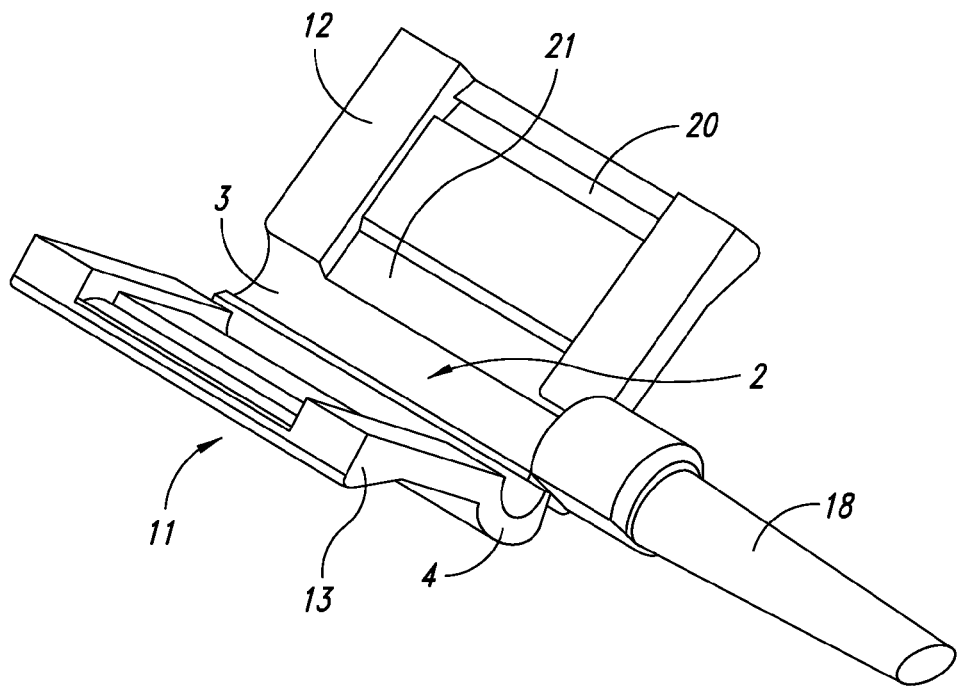
FIG. 1 shows a perspective view of a practical example of the invention which shows a lens receiving compartment in the form of a cartridge, which compartment constitutes an integral part of a lens injector.
Figure 2:
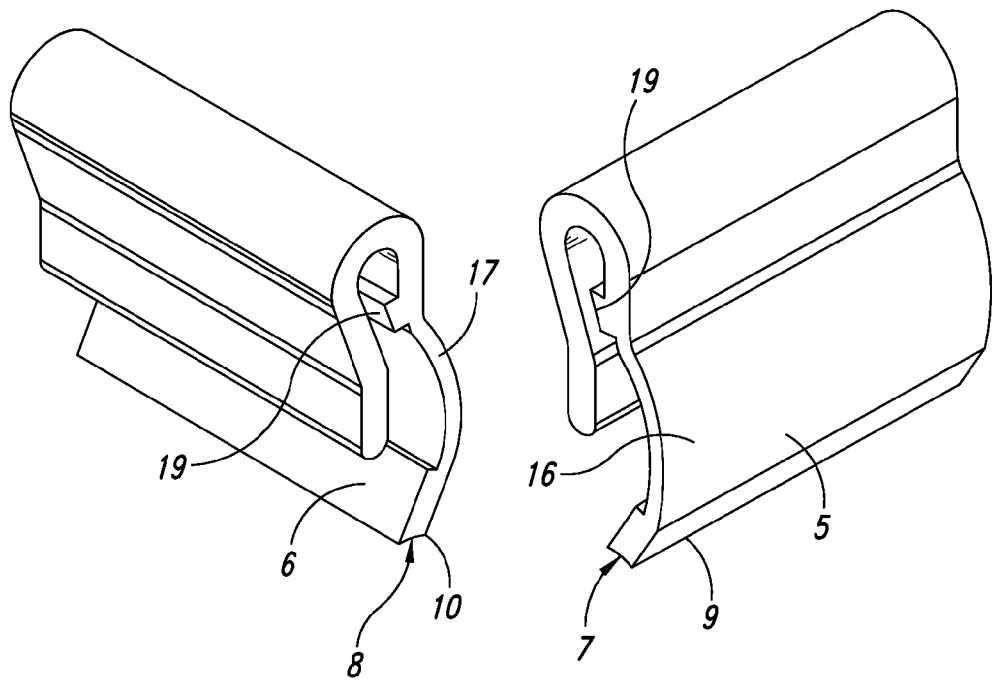
FIG. 2 shows a perspective view of holding elements that are to be attached to lens receiving parts of the lens receiving compartment shown in FIG. 1.

The holding elements which, as shown in FIG. 2, have the form of braces are attached to the attachment points 14, 15 on the wings 12, 13. The attachment is implemented in the form of a form-fitting lock. To this end, projections 19 can be disposed on the holding elements 5, 6, which projections extend into recesses 20 on the inside surface of the wings 12, 13 so as to produce a form-fitting lock.

On the ends facing the lens receiving compartment 2, the holding elements have stop faces 7 and 8. The holding elements fitted with these stop faces 7, 8 form a holding device for the intraocular lens 1 that is disposed inside the lens receiving compartment 2. In the starting position schematically shown in FIG. 3, the unfolded intraocular lens 1 is contained in the lens receiving compartment 2 in a tension-free state. The stop faces 7, 8 are located above diametrical edge regions of the intraocular lens 1 and, in the configuration shown in FIG. 3, prevent the lens from falling in the upward direction out of the compartment. In the starting position shown in FIG. 3, the diametrical edge regions of the lens rest on the lower surface on areas of the lens receiving parts 3 and 4. These support areas, together with the stop faces 7, 8, form chambers or channels for receiving the diametrical lens edge regions, the cross section of which chambers or channels is approximately triangular. On the lower surface along its longitudinal center, the intraocular lens 1 can be additionally supported by the receiving parts 3, 4 approximately in the region of the swivel axis, by means of which these receiving parts are connected to each other. This ensures that the unfolded lens is securely positioned in the lens receiving compartment 2. In the configuration shown in FIG. 3, the intraocular lens 1 can be sterilized and kept ready for use. To this end, the configuration shown in FIG. 3 can be kept ready for use or can be stored in a sleeve or container 8. This configuration can also be transported and shipped.

Figure 4:
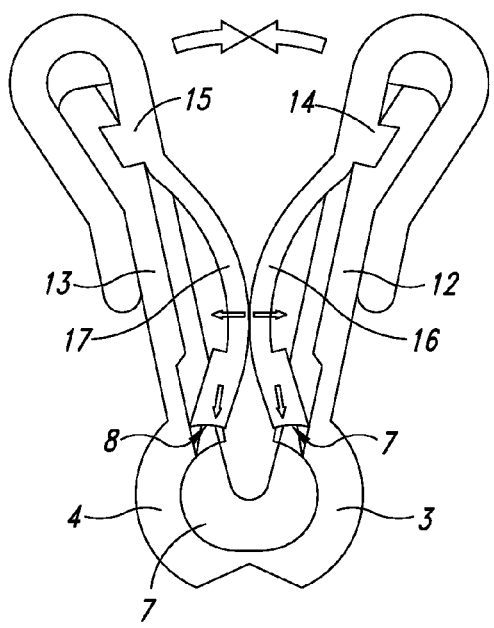
FIG. 4 shows an intermediate position of the components of the lens receiving compartment while the lens is being folded.
Figure 5:
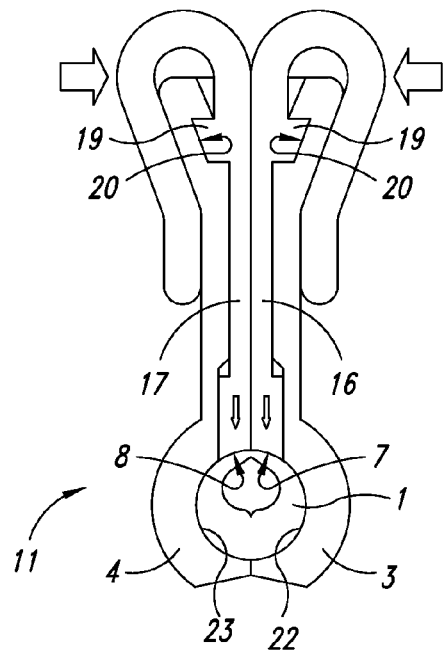
FIG. 5 shows the final position of the components of the practical example with the lens folded in the lens receiving compartment.

The holding elements 5, 6 are resilient and to this effect have bed parts 16, 17 in the form of small plates disposed between the stop faces 7, 8 and the attachment points 14, 15. As the wings 12, 13 are moved toward each other, the bent parts 16, 17 come into contact with each other, as shown in FIG. 4. As the bent parts 16, 17 continue to be swiveled toward each other, these parts are made to assume a stretched-out linear shape, as shown in FIG. 5. In the course of this swiveling movement, the lens receiving parts 3, 4 are moved toward each other, and the lens contained in the lens receiving compartment 2 is initially compressed and subsequently folded. During the initial compression of the lens, inside edges which run approximately parallel to the longitudinal center of the intraocular lens 1 come into contact with the lens area lying above. These inside edges 9, 10 are located at a distance of approximately 1.0 mm from the respective lens edge. As the wings 12, 13 are moved toward each other, the edges 9, 10 exert pressure on the upper surface of the intraocular lens 1 so that this lens is preliminarily folded downwardly along its longitudinal center. As the wings 12, 13 are further pushed toward each other, as shown in FIG. 4, the lens is pushed into the direction of the bottom of the lens receiving compartment 2 and is made to assume the folded or rolled-up shape as shown in FIG. 5. In the course of this procedure, the stop faces 7, 8 exert pressure on the diametrical edges of the lens, which pressure is generated during the phase in which the bent parts 16, 17 of the holding elements 5, 6 are made to assume the linear stretched-out shape shown in FIG. 5. At the same time, the stop faces 7, 8 move out of the positions (FIG. 3) in which they are retracted in the indentations 21 in the lens receiving parts 3, 4 or wings 12, 13 or out of the outer positions into the direction toward the inside of the lens receiving compartment and reach the end position shown in FIG. 5. In this end position, the preferably concave stop faces 7, 8, in cooperation with the boundary surfaces 23 of the lens receiving parts 3, 4, form a flush cylindrical boundary surface of the lens receiving compartment 2 in which the folded or rolled-up lens 1 is located. The cylindrical cross section can be circular or, depending on the type of lens used, it can also have a different shape.

As shown in the practical example, the lens receiving compartment can be an integral part of a cartridge 11 which forms part of an injector with an injection cannula 18. This cartridge 11 can be inserted into the injector or can be molded in one piece with the injector. To this effect, both ends of the lens receiving compartment 2 are open in the direction of implantation. One of the openings opens out into the injection cannula 18 and the opening on the other end offers access for an injector plunger (not shown), by means of which the folded or rolled up lens contained in the lens receiving compartment is implanted into the eye through the injection cannula 18, for example, during cataract surgery. Examples of a suitable injector plunger and injector are known from EP 1 438 929 A1.

In the practical example shown in FIGS. 6-9, identical components or components having the same function are designated by reference numeral identical to the ones used in the practical example described previously. The practical example described in FIGS. 6-9 is special in that stops 27 are disposed on the holding elements 5 and 6 in the immediate vicinity of the stop faces 7 and 8. When the lens compartment parts are closed, i.e., in the state shown in FIG. 5, these stops 27 lie close to the stops 26 which are disposed in the immediate vicinity of the lens receiving compartment 2 on the lens receiving parts 3, 4 or the inside ends of the wings 12, 13. This determines the accurate positioning of the stop faces 7, 8 which are integral parts of the boundary surfaces that define the inside chamber of the lens receiving compartment. Given the short distance between the stop faces 7, 8 and the stops 26, 27, manufacturing tolerances of the holding elements 5, 6 have no effect. Thus, as shown in FIG. 5, a flush inside boundary surface of the closed lens receiving compartment 2 with the boundary surfaces 22, 23 of the lens receiving parts is ensured.

In the practical example illustrated in FIGS. 6-9, the holding elements 5, 6 are attached by means of ends of the holding elements 5, 6 that are bent to form a U-shape. These U-shaped bent ends 24 are inserted into openings 25 of the wings 12, 13. As a result, two clamp-fitting connections are produced on each wing 12, 13, by means of which clamp-fitting connections on the upper ends of the holding elements 5, 6 are attached to the wings 12, 13.

In addition, in the practical example of FIGS. 6-9, a joining latch bar 31 is disposed on the upper end of wing 12, which joining latch bar protrudes in the direction of the other wing 13. Disposed on the lower surface of the joining latch bar 31 is a latch projection 30 which in closed lens receiving compartment 2 engages in a latch groove 29 on the free end edge of wing 13. In the practical example illustrated, the latch projection 30 and the latch groove 29 are constructed in the form of continuous components which extend across the entire length of the wings 12, 13. It is, however, also possible to dispose a plurality of latch projections and latch grooves on the wings 12, 13. When the lens receiving compartment 2 is closed, which compartment in the practical example of FIGS. 6-9 again is an integral part of a cartridge, a latch connection for the cartridge is obtained, which facilitates handling. To move the practical example in FIGS. 6-9 from the open position into the closed position, steps identical to those explained in the example according to FIGS. 3-5 are carried out.

FIGS. 6-9 show a device for folding or rolling up an intraocular lens (1) that is to be implanted into an eye, with a lens receiving compartment (2) that is formed by two swivel-connected lens receiving parts (3, 4). The lens receiving compartment (2) is to be moved from an open position for receiving the lens (1), in which the lens is unfolded, into a closed position for folding or rolling up the lens (1) by swiveling the lens receiving parts (3, 4) relative to each other. The lens receiving parts (3, 4) are swiveled relative to each other with a holding device, which is attached to the lens receiving parts (3, 4), for holding the lens (1) when the lens receiving compartment (2) is open and the lens receiving parts (3, 4) are swiveled relative to each other. The holding device comprises two holding elements (5, 6), one of which holding elements (5) is attached to a lens receiving part (3) and the other holding element (6) is attached on the other lens receiving part (4). Stop faces (7, 8) for diametrical edge regions of the unfolded lens (1) contained in the open lens receiving compartment (2) are disposed on the holding elements (5, 6). When the receiving compartment (2) is closed, the stop faces (7, 8), in cooperation with the boundary surfaces (22, 23) that are formed by the lens receiving parts (3, 4), enclose the lens receiving compartment (2). The two holding elements (5, 6) are resilient and the lens receiving parts (3, 4) comprise wings (12, 13) to which the holding elements (5, 6) are resiliently attached.

LIST OF REFERENCE NUMERALS

1 Intraocular lens
2 Lens receiving compartment
3, 4 Lens receiving parts
5, 6 Holding elements
7, 8 Stop faces
9, 10 Inside edges
11 Cartridge
12, 13 Wings
14, 15 Attachment points
16, 17 Bent parts
18 Injection cannula
19 Projections
20 Recesses
21 Indentations
22, 23 Boundary surfaces
24 Ends of the holding elements bent to form a U-shape
25 Openings in the wings
26, 27 Stops
28 Container or sleeve
29 Latch groove
30 Latch projection
31 Joining latch bar

The invention claimed is:

1. A device for folding or rolling up an intraocular lens that is to be implanted into an eye, comprising:
a lens receiving compartment that is formed by swivel-connected first and second lens receiving parts, which lens receiving compartment is configured to be moved from an open position for receiving the lens, in which the lens is unfolded, into a closed position for folding or rolling up the lens by swiveling the lens receiving parts relative to each other, the first and second lens receiving parts having respective boundary surfaces; and
a holding device attached to the lens receiving parts and configured to hold the lens when the lens receiving compartment is open and the lens receiving parts are swiveled relative to each other, wherein:

the holding device comprises first and second holding elements attached to the first and second lens receiving parts, respectively, the first and second holding elements have respective stop faces configured to contact diametrical edge regions of the unfolded lens contained in the open lens receiving compartment the stop faces, in cooperation with the boundary surfaces of the lens receiving parts, enclose the lens receiving compartment when the receiving compartment is closed;

the first and second holding elements are resilient; and the first and second lens receiving parts respectively comprise first and second wings respectively resiliently attached to the holding elements.

2. The device as in claim 1, wherein the holding elements are configured to, as the lens receiving parts are swiveled relative to each other, exert a pressure, via the respective stop faces, on the diametrical edge regions of the lens.

3. The device as in claim 1, wherein the stop faces have respective inner edges configured to initiate the folding procedure along a longitudinal center of the lens, which center runs substantially parallel to the inner edges.

4. The device as in claim 1, wherein the holding device is configured to movably guide the stop faces between an outer position when the lens receiving compartment is open and an inner position when the lens receiving compartment is closed.

5. The device as in claim 1, wherein:

the wings have respective free ends with respective attachment points to which the first and second holding elements are respectively attached; and the first and second holding elements have respective resiliently bent parts between the respective attachment points and the respective stop faces.

6. The device as in claim 5, wherein the resiliently bent parts of the holding elements are configured to move into stretched-out linear positions, during movement into the closed position of the receiving compartment, and exert a pressure on the lens via the respective stop faces of the holding elements.

7. The device as in claim 5, wherein the attachment points are disposed on respective sides of the wings that are oriented toward each other.

8. The device as in claim 1, wherein the holding elements are respectively attached to the lens receiving parts or to the wings by at least one of a form-fitting lock, a clamp-fitting lock, and hinges.

9. The device as in claim 1, wherein the stop faces are concave.

10. The device as in claim 1, wherein the holding elements have the form of braces.

11. The device as in claim 1, wherein the holding elements have respective portions adjacent to the stop faces that are configured to move on the lens receiving parts under guidance of the lens receiving parts.

12. The device as in claim 1, wherein the lens receiving compartment is an integral part of a cartridge, and said lens receiving compartment has an open ends when the lens receiving compartment is in the closed position.

13. The device as in claim 1, comprising an injection cannula, wherein the lens receiving compartment has a first open end that opens out into the injection cannula and a second open end that offers access for a propelling plunger for pushing the rolled-up or folded lens contained in the lens receiving compartment through the injection cannula.

14. The device as in claim 1, wherein the lens receiving parts have respective stops on which the holding elements are respectively supported when the lens receiving compartment is closed.

15. The device as in claim 14, wherein the stops are disposed in close vicinity to the lens receiving compartment.

16. The device as in claim 1, comprising a container or sleeve that houses the lens receiving compartment and the holding device, wherein the intraocular lens, which, when unfolded and free from tension, is disposed in the lens receiving compartment, laterally held on the stop faces (7, 8), and is suitable to be stored in the container or a sleeve in readiness for use.

17. The device as in claim 1, comprising a latch connection configured to keep the lens receiving parts closed.

18. The device as in claim 17, wherein the latch connection includes first and second latch components disposed on free ends of the wings, respectively.

* * * * *